(12) United States Patent
Morisawa (10) Patent No.: US 11,545,244 B2
(45) Date of Patent: Jan. 3, 2023

(54) WATER PRESCRIBING SYSTEM AND WATER PRESCRIBING PROGRAM

(71) Applicant: NIHON TRIM CO., LTD., Osaka (JP)

(72) Inventor: Shinkatsu Morisawa, Osaka (JP)

(73) Assignee: NIHON TRIM CO., LTD., Osaka (JP)

( * ) Notice: Subject to any disclaimer, the term of this patent is extended or adjusted under 35 U.S.C. 154(b) by 7 days.

(21) Appl. No.: 17/044,563

(22) PCT Filed: Apr. 9, 2019

(86) PCT No.: PCT/JP2019/015463
§ 371 (c)(1),
(2) Date: Oct. 1, 2020

(87) PCT Pub. No.: WO2019/198711
PCT Pub. Date: Oct. 17, 2019

(65) Prior Publication Data
US 2021/0098100 A1    Apr. 1, 2021

(30) Foreign Application Priority Data

Apr. 11, 2018 (JP) .............................. JP2018-076031

(51) Int. Cl.
*G16H 20/00* (2018.01)
*G16H 40/00* (2018.01)

(52) U.S. Cl.
CPC ............ *G16H 20/00* (2018.01); *G16H 40/00* (2018.01)

(58) Field of Classification Search
None
See application file for complete search history.

(56) References Cited

U.S. PATENT DOCUMENTS

| | | | |
|---|---|---|---|
| 2008/0077430 A1* | 3/2008 | Singer | A61M 15/0075 705/2 |
| 2016/0196389 A1* | 7/2016 | Moturu | G16H 50/20 705/2 |
| 2016/0284004 A1 | 9/2016 | Taylor | |
| 2018/0004913 A1 | 1/2018 | Ghasemzadeh et al. | |
| 2018/0353670 A1* | 12/2018 | Kommala | G16H 20/10 |

FOREIGN PATENT DOCUMENTS

| | | | |
|---|---|---|---|
| CN | 103760875 A | * | 4/2014 |
| JP | 3849644 B2 | * | 11/2006 |
| JP | 2007-295881 A | | 11/2007 |
| JP | 2015-127301 A | | 7/2015 |
| JP | 2016-165667 A | | 9/2016 |
| JP | 2018-045413 A | | 3/2018 |
| WO | 2016168120 A1 | | 10/2016 |

OTHER PUBLICATIONS

Sarkar, R. "The Efficacy and Tolerability of Electrolyzed Oxidized Water in Treating Mild to Moderate Acne," 2004, Cosmetic Dermatology, vol. 17, No. 2, pp. 93-106. (Year: 2004).*
Jennifer J. Otten et al: "Dietary Reference Intakes: The Essential Guide to Nutrient Requirements. Institute of Medicine", Dec. 31, 2006, XP055450504, Washington, DC.

* cited by examiner

*Primary Examiner* — Lena Najarian
(74) *Attorney, Agent, or Firm* — Muncy, Geissler, Olds & Lowe, P.C.

(57) ABSTRACT

A water prescribing system 1 is provided with a state storage unit 21 which stores a state variable relating to a physical constitution and health condition for each of a plurality of persons including a user, and a prescription unit 22 which creates a prescription of water suitable for the user based on the state variable.

7 Claims, 7 Drawing Sheets

| | user 1 | user 2 | user 3 | user 4 | user 5 | ... |
|---|---|---|---|---|---|---|
| age | 25 | 38 | 33 | 56 | ... | ... |
| sex | male | male | female | male | ... | ... |
| height (cm) | 173 | 183 | 156 | ... | ... | ... |
| weight (kg) | 67 | 72 | 60 | ... | ... | ... |
| waist circumference (cm) | 90 | 93 | 65 | ... | ... | ... |
| body temperature (°C) | 36.4 | 35.9 | 35.7 | ... | ... | ... |
| blood pressure (mmHg) | 120-100 | 125-105 | 115-95 | ... | ... | ... |
| blood test : blood glucose level (mg/dL) | 85 | 90 | 95 | ... | ... | ... |
| body fat percentage (%) | 17 | 22 | 19 | ... | ... | ... |
| visceral fat mass (cm²) | 8 | 9 | 11 | ... | ... | ... |
| basal metabolism (kcal/kg/day) | 26 | 27 | 22 | ... | ... | ... |
| medical history | none | kidney disease | none | ... | ... | ... |
| exercise history | baseball | volleyball | golf | ... | ... | ... |
| alcohol intake (mL per day) | 200 | 100 | 0 | ... | ... | ... |
| tobacco intake (per day) | 0 | 10 | 0 | ... | ... | ... |
| genetic information | *** | *** | *** | ... | ... | ... |
| ... | ... | ... | ... | ... | ... | ... |

FIG.4

| | user 1 | user 2 | user 3 | user 4 | user 5 | ... |
|---|---|---|---|---|---|---|
| pH value | 7.8 | 8.3 | 7.5 | ... | ... | ... |
| dissolved hydrogen concentration (ppb) | 1000 | 1300 | 800 | ... | ... | ... |
| redox potential (mV) | -300 | -400 | -350 | ... | ... | ... |
| temperature (°C) | 18 | 18 | 22 | ... | ... | ... |
| mineral component | Ca, K, Mg | Ca, Mg | Ca, K, Mg | ... | ... | ... |
| water intake amount (mL) | 600 | 800 | 700 | ... | ... | ... |
| ... | ... | ... | ... | ... | ... | ... |
| ... | ... | ... | ... | ... | ... | ... |

WATER PRESCRIBING SYSTEM AND WATER PRESCRIBING PROGRAM

TECHNICAL FIELD

The present invention relates to a water prescribing system and a water prescribing program for prescribing water suitable for a user.

BACKGROUND ART

In recent years, with the increase in health consciousness, the demand for dissolved hydrogen water, in which hydrogen molecules are dissolved in water, has been increasing. The dissolved hydrogen water is produced by an electrolytic water production device that electrolyzes water, for example. The electrolytic water production device is configured to be able to produce electrolyzed water having various dissolved hydrogen concentrations and pH values by controlling an electrolytic current for electrolysis, for example (see Patent Document 1, for example).

By the way, a physical constitution, health condition, and the like of the users who use the electrolytic water production device are various, and the water suitable for each user is different. However, it has been difficult for the user to easily know the water suitable for his or her body, and it has been necessary to seek guidance from a doctor or a specialist.

CITATION LIST

Patent Literature

Patent Literature 1: Japanese Unexamined Patent Publication No. 2016-165667

SUMMARY OF THE INVENTION

Problems to be Solved by the Invention

The present invention has been devised in view of the above circumstances, and has as its main purpose to provide a water prescribing system and a water prescribing program for prescribing water suitable for users.

Means for Solving the Problem

The present invention is a water prescribing system including a state storage unit which stores a state variable relating to a physical constitution and health condition with respect to each of a plurality of persons including a user, and a prescription unit which creates a prescription suitable for the user based on the state variable. Here, the user may include not only a person who is currently using the water prescribing system, but also a person who plans to use or may possibly use the system in the future. Further, the state storage unit may be configured to store the state variable of the user only.

In the water prescribing system, it is preferred that the state variable includes at least one of age, sex, height, weight, waist circumference, body temperature, blood pressure, blood test results, body fat percentage, visceral fat mass, basal metabolism, medical history, exercise history, alcohol intake, tobacco intake, and genetic information of each user.

In the water prescribing system, it is preferred that the prescription includes at least one of a pH value, a dissolved hydrogen concentration, a redox potential, a temperature, a mineral component, and an intake amount of the water.

In the water prescribing system, it is preferred that the prescription unit has a model storage unit which stores a learning model for creating the prescription suitable for the state variable and applies the state variable of each user to the learning model to creates the prescription.

In the water prescribing system, it is preferred that the state storage unit stores transition of the state variable of the user after ingesting the water according to the prescription, and the prescription unit has a value calculation unit for calculating value function relating to effect of the water on the state variable based on the transition of the state variable and an update unit for updating the prescription based on the value function.

In the water prescribing system, it is preferred that the prescription unit further includes a reward calculation unit for calculating a reward based on the transition of the state variable, and the value calculation unit updates the value function based on the reward.

In the water prescribing system, it is preferred that the reward calculation unit gives the positive reward when the state variable has changed favorably with regard to each user, and gives the negative reward when the state variable has changed poorly with regard to each user.

In the water prescribing system, it is preferred that the learning model includes a neural network.

In the water prescribing system, it is preferred that the state storage unit and the prescription unit are provided in a server which is connectable to the Internet.

It is preferred that the water prescribing system further includes an electrolytic water production device for producing electrolytic water by electrolyzing water and that the electrolytic water production device is connected with the server and produces the electrolytic water according to the prescription.

It is preferred that the water prescribing system further includes a transmission means which is connected to the server and transmits the state variable to the server.

Further, the present invention is a water prescribing program for causing a computer to execute a step of creating a prescription of water suitable for a user based on a state variable relating to a physical constitution and health condition stored in advance for each of a plurality of persons including the user. Here, the user may include not only a person who is currently using the water prescribing system, but also a person who plans to use or may possibly use the system in the future.

In the water prescribing program, it is preferred that the water prescribing program is for causing the computer to further execute a step of storing transition of the state variable of the user after ingesting the water according to the prescription, a step of calculating a value function relating to effect of the water on the state variable based on the transition of the state variable, and a step of updating the prescription based on the value function.

Advantageous Effects of the Invention

The water prescribing system of the present invention includes the state storage unit which stores the state variable relating to the physical constitution and the health condition with respect to each of a plurality of persons including the user, and the prescription unit which creates the prescription suitable for the user based on the state variable. Therefore, the user can easily know the water suitable for his or her body by the prescription automatically created by the prescription unit without getting a diagnosis of a doctor or a specialist. Thereby, the health of the user is easily maintained and promoted.

DESCRIPTION OF THE PREFERRED EMBODIMENT

An embodiment of the present invention will now be described below in conjunction with accompanying drawings.

Figure 1:
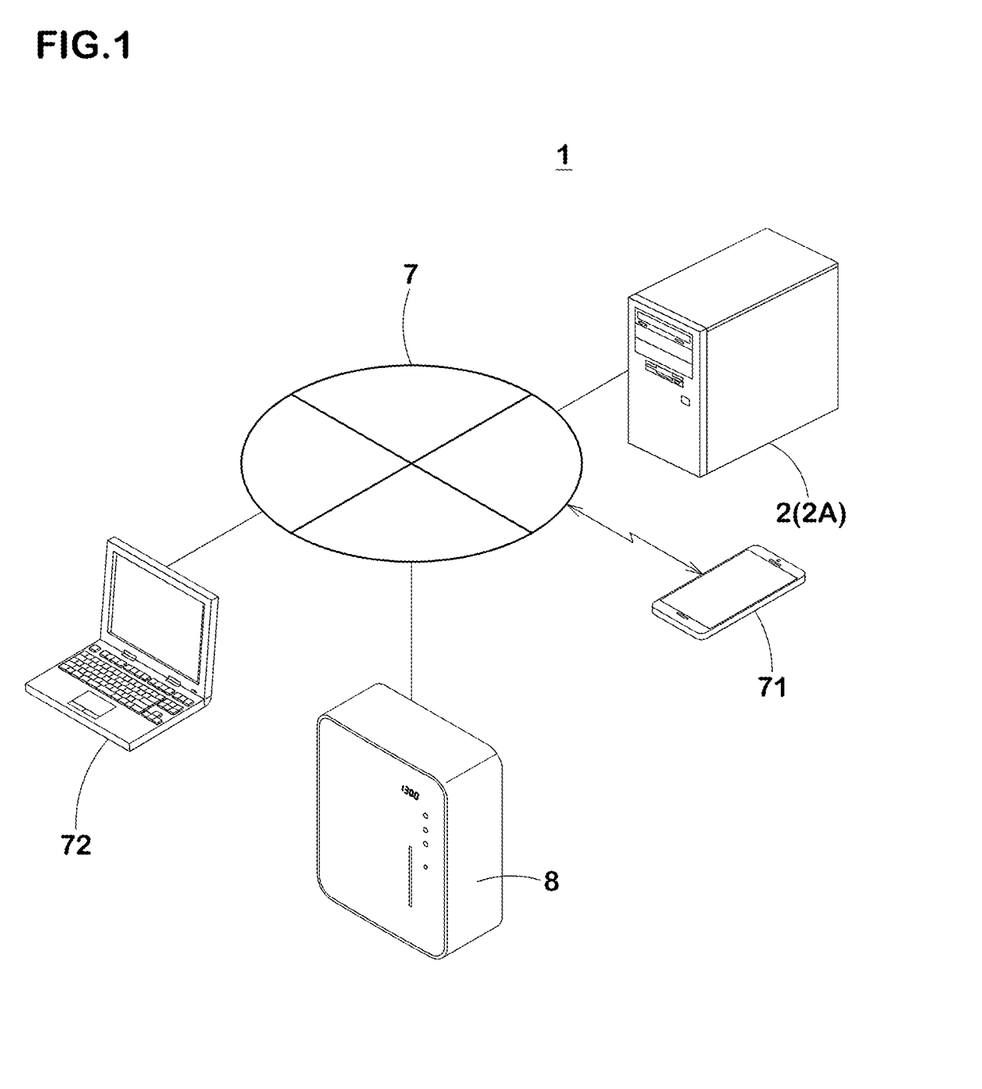
FIG. 1 A diagram showing a schematic configuration of a water prescribing system according to an embodiment of the present invention.

FIG. 1 shows a schematic configuration of a water prescribing system 1 of the present embodiment. The water prescribing system 1 includes a server 2 that provides services to users. A computer device is used for the server 2.

Figure 2:
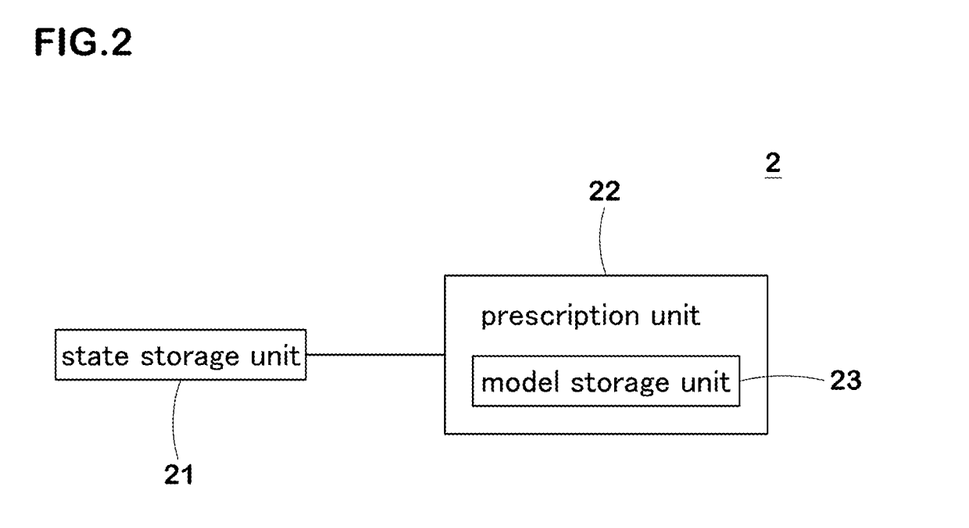
FIG. 2 A block diagram showing a configuration of a server of FIG. 1.

FIG. 2 is a block diagram showing the configuration of the server 2. The server 2 includes a state storage unit 21 which stores state variables and a prescription unit 22 which creates a prescription. The state storage unit 21 and the prescription unit 22 may be provided separately in a plurality of computer devices.

Figure 3:
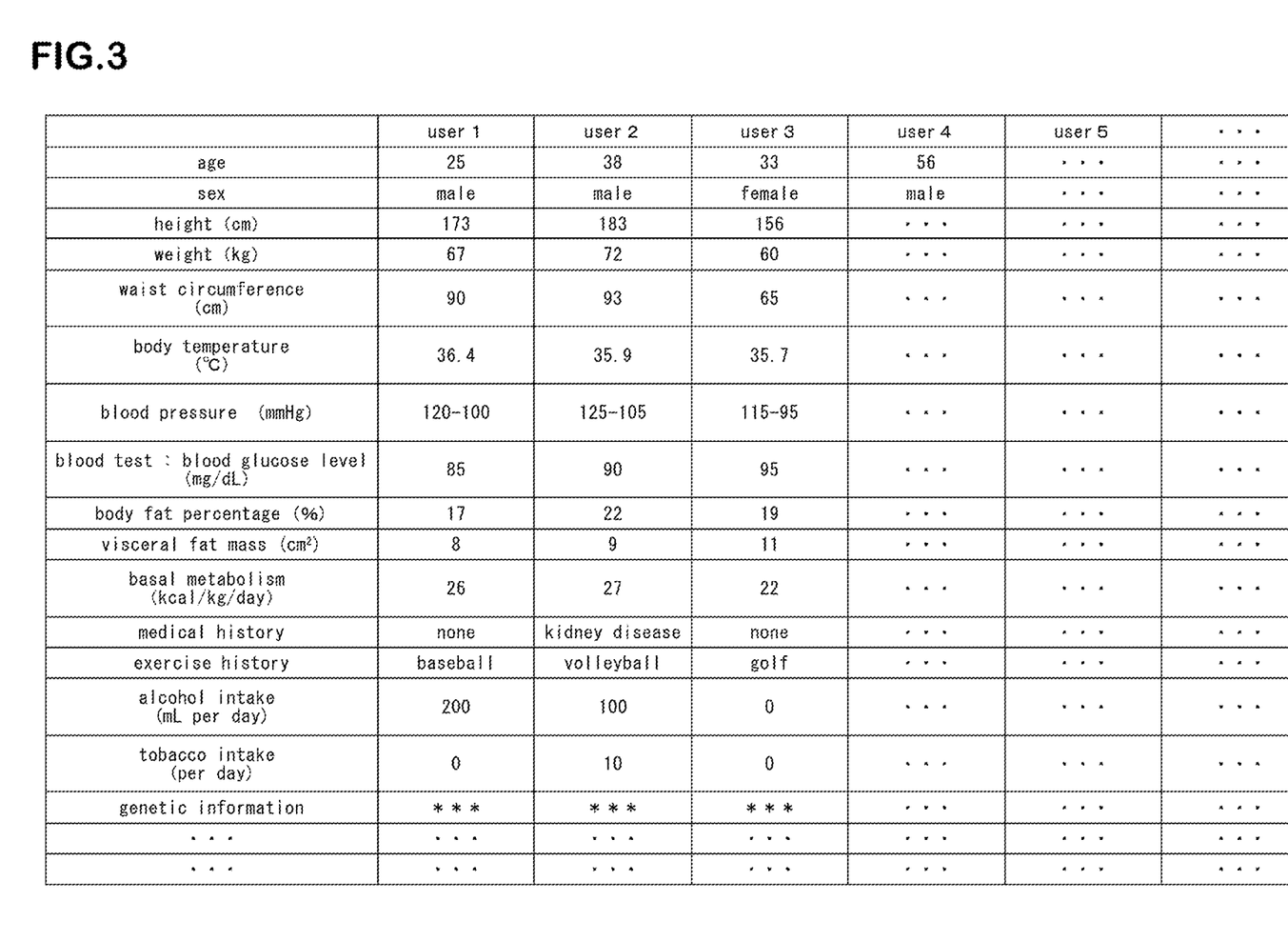
FIG. 3 A diagram showing state variables.

FIG. 3 shows the state variables. The state variables are information (data) about a physical constitution and health condition, and are collected for each of a plurality of persons including a user. The state variables include, for example, at least one of age, sex, height, weight, waist circumference, body temperature, blood pressure, blood test results, body fat percentage, visceral fat mass, basal metabolism, medical history, exercise history, alcohol intake, tobacco intake, and genetic information of each person. The state variables may include other variables. The state variables are managed and utilized as a database, for example.

The blood test results include at least one of AST (GOT), ALT (GPT), γ-GTP, HDL cholesterol, LDL cholesterol, and blood glucose level, for example. Other variables may be included in the blood test results.

In the water prescribing system 1, it is preferred that a large amount of state variables be collected and stored in the state storage unit 21 for creating a prescription which will be described later. Therefore, the state storage unit 21 may store state variables of other persons than the user. For the state storage unit 21 configured as such, a large-capacity data storage means such as a hard disk device or an SSD (Solid State Drive) is suitably used, for example.

Figure 4:
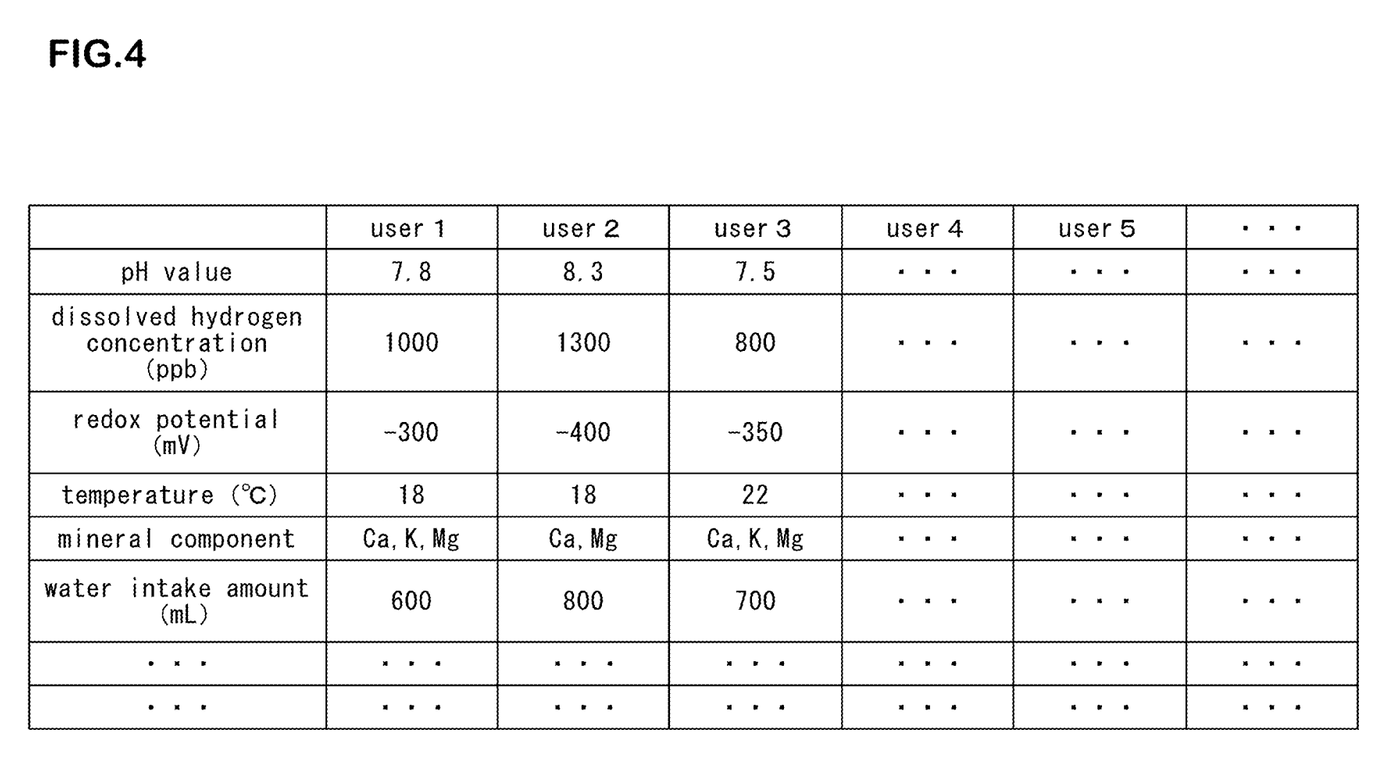
FIG. 4 A diagram showing prescriptions.

FIG. 4 shows a prescription. The prescription is water prescription data suitable for each user of the water prescribing system 1. The prescription includes, for example, at least one of pH value of water, dissolved hydrogen concentration, redox potential, temperature, mineral component, and water intake. The prescription may include other prescription data. The prescription is not limited to a form printed on paper, and may be electronic data that can be displayed on a liquid crystal display, for example. The prescription is created for each user by the prescription unit 22 based on the state variables. The prescription is managed and utilized as a database, for example.

The prescription unit 22 includes, for example, a CPU (Central Processing Unit) which executes various arithmetic processes, information processing, and the like, a program which controls the operation of the CPU, and a memory which stores various information, and the like. The program may be stored in the hard disk device or the like. That is, the CPU, the memory, and the like function as the prescription unit 22 by a program stored in the memory, the hard disk device, or the like. It should be noted that in addition to the CPU or in place of the CPU, a GPU (Graphics Processing Unit) that excels in image data processing may be used for the prescription unit 22.

The prescription unit 22 creates a prescription for each user based on the state variables stored in the state storage unit 21 and based on the medical knowledge including the rule of thumb. The prescription created by the prescription unit 22 is stored in the hard disk device or the like of the server 2.

The medical knowledge includes knowledge and insights of doctors, papers, and so on. For example, water intake according to age, sex, height, weight, blood glucose level, exercise amount, alcohol intake, tobacco intake, and the like is proposed. Further, the temperature according to body temperature, sex, and basal metabolism is proposed. Furthermore, the mineral component according to a medical history is proposed. More specifically, water in which potassium is limited by using a filter or the like is proposed to a user who is suffering from kidney disease. Furthermore, pH value, dissolved hydrogen concentration, and redox potential may be proposed according to blood pressure, blood glucose level, body fat percentage, visceral fat mass, basal metabolism, medical history, exercise history, alcohol intake, and genetic information. The relationship between the state variables and recommended water based on these medical findings is stored in advance in the hard disk device and the like of the server 2 and is referred to when the prescription unit 22 creates a prescription.

According to the present water prescribing system 1, the prescription unit 22 creates a prescription of water suitable for the user based on the state variables stored in the state storage unit 21. Therefore, the user can easily know the water suitable for his or her body by the prescription automatically created by the prescription unit 22 without getting a diagnosis of a doctor or a specialist. Thereby, the health of the user is easily maintained and promoted.

It is preferred that the prescription unit 22 includes a model storage unit 23 which stores a learning model for creating a water prescription that matches the state variable.

Figure 5:
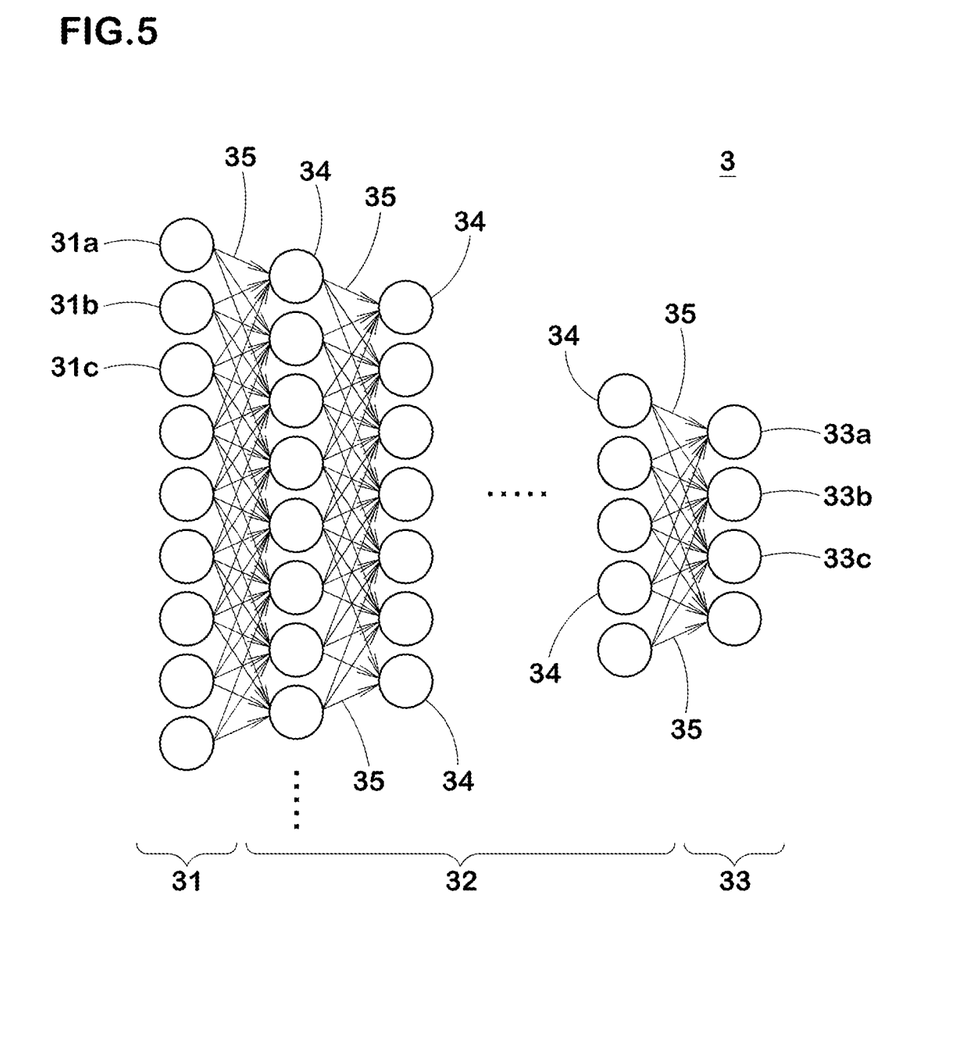
FIG. 5 A diagram showing a learning model.

FIG. 5 shows a learning model 3. The learning model 3 is generated by deep learning (deep machine learning) using artificial intelligence (AI), for example. In the present embodiment, the learning model 3 is generated by calculation by the server 2 constituting the water prescribing system 1 and is stored in the hard disk device or the like of the server 2. The learning model 3 may be generated by calculation by another computer device provided outside the water prescribing system 1 and input to the server 2, for example.

The learning model 3 is defined by an intermediate layer 32 generated by machine learning with the state variables $31a$, $31b$, $31c$, ... as an input layer 31 and the prescriptions $33a$, $33b$, $33c$, ... as an output layer 33.

The state variables $31a$, $31b$, $31c$, ... Of the input layer 31 are associated to any of the prescription $33a$, $33b$, $33c$, ... of the output layer 33 based on medical knowledge.

That is, the state variables 31a, 31b, 31c, . . . are stored in the hard disk device in a state in which they are associated with any of the prescription 33a, 33b, 33c, . . . and can be used as training data for deep learning.

The intermediate layer 32 includes combinations of a plurality of neurons (nodes) 34 hierarchized in multiple stages and optimized weighting coefficients 35 (parameters). Each of the neurons 34 is connected by weighting coefficients 35. The intermediate layer 32 configured as such is called a neural network. That is, the learning model 3 of the present embodiment includes a neural network.

For example, for each neuron, the weighting coefficients 35 are learned by adjusting the weighting coefficients 35 so that the difference between an output (y) when an input (x) is input and a true output (y) (training data) is decreased. Such a learning method is called an error back propagation method (Backpropagation). The learning model 3 is generated by determining each of the neurons 34 and each of the weighting coefficients 35.

The prescription unit 22 applies the state variables of each user to the learning model 3 generated as described above, and creates a water prescription suitable for each user. Thereby, a water prescription suitable for the physical constitution, medical history, physical condition, and the like of each user is automatically created. In addition, since the learning model 3, which is generated by processing an enormous amount of data by artificial intelligence, is used in creating a prescription, water suitable for each user can be easily prescribed without relying only on the past experience of a doctor.

It is preferred that the prescription unit 22 is configured to update the learning model 3 by continuous deep learning even after the user ingests water according to the prescription. In this case, the state storage unit 21 stores state variables of the user obtained after the user ingests the water according to the prescription. Then the prescription unit 22 updates the learning model 3 by deep learning based on the state variables obtained after each user ingests water. In this deep learning, the learning model 3 may be updated by unsupervised learning.

Figure 6:
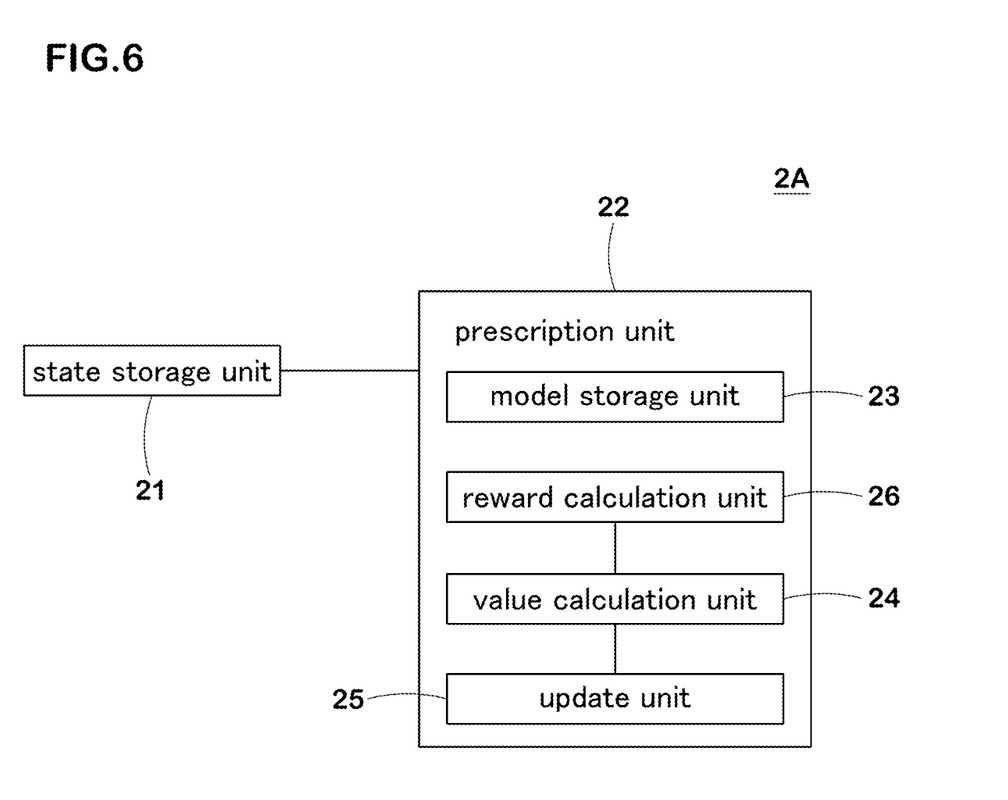
FIG. 6 A block diagram showing a configuration of a modification of the server of FIG. 1.

FIG. 6 shows a server 2A which is a modification of the server 2. The server 2A is different from the server 2 in that the prescription unit 22 includes a value calculation unit 24, an update unit 25, and a reward calculation unit 26. For the portions of the server 2A that are not described below, the configuration of the server 2 described above can be employed.

In the server 2A, the prescription is updated by reinforcement learning using value function and optimized for each user.

The "reinforcement learning" is a technique for learning appropriate actions based on the interaction that actions have on environment by the computer device learning the actions. In the present embodiment, the "action" means that the user ingests water according to a prescription created by the server 2A. Further, the "environment" is state variables of each user after ingesting water according to a prescription. In the server 2A, the reinforcement learning is started with the state where the prescription is created by the learning model 3 as an initial state, but the reinforcement learning may be started with the state where the prescription created by a doctor or an expert is present as the initial state.

The "value function" is a function that represents the interaction that the actions have on the environment. The value function is represented by a function in which state, actions, and reward are the variables. The action with the highest value can be selected by the value function. The value function in the present embodiment corresponds to a function related to the effect of water ingested based on a prescription on the state variables.

In the water prescribing system 1 including the server 2A, the transition of the state variables of each user after ingesting water according to the prescription is input to the server 2A. The transition of the state variables is input by the user or administrator of the water prescribing system 1 and stored in the state storage unit 21.

The value calculation unit 24 calculates a value function based on the transition of the state variables stored in the state storage unit 21. The update unit 25 updates the prescription based on the value function. More specifically, the update unit 25 updates the prescription so that the value function is maximized. As a result, the user can ingest water that is more suitable for his or her body. It should be noted that the update unit 25 may be configured to update the prescription by updating the learning model 3 shown in FIG. 5. In this case, the accuracy of the learning model 3 is further improved.

It is preferred that, in the server 2A, the prescription unit 22 further includes the reward calculation unit 26 that calculates a reward based on the transition of the state variables. The reward calculation unit 26 gives a positive reward when the state variables of each user have changed favorably, and gives a negative reward when the state variables of each user have changed poorly, for example. The degree of reward is calculated by the reward calculation unit 26 in accordance with, for example, predetermined weighting of each of the state variables and variation amount of the state variables. Thereby, the reward is calculated appropriately and easily according to the transition of the state variables.

The reward calculated by the reward calculation unit 26 is input to the value calculation unit 24. Then, the value calculation unit 24 updates the value function based on the reward. The update unit 25 then learns to maximize the value function and updates the prescription. This makes it possible to create prescriptions that appropriately reflect the transition of the state variables.

As shown in FIG. 1, in the water prescribing system 1, it is preferred that the server 2 or 2A is connected to the Internet 7. In this case, a terminal device such as a mobile information terminal 71 and a personal computer 72 that are owned and managed by the user or the administrator of the water prescribing system 1 and can be connected to the Internet 7 can also be included in the water prescribing system 1. That is, the user or the administrator can access the server 2 or 2A from the terminal device such as the mobile information terminal 71 and the personal computer 72 owned and managed by the user or the administrator via the Internet 7 to transmit the state variables and the like to store them in the state storage unit 21. In this case, the terminal device such as the mobile information terminal 71 and the personal computer 72 functions as a transmission means.

The prescription created by the prescription unit 22 is stored in the hard disk device or the like of the server 2 or 2A. Each user, for example, operates the mobile information terminal 71 or personal computer 72 to access the servers 2 and 2A via the Internet 7 to receive and browse the prescription stored in the hard disk device or the like. Can do. In this case, terminal devices such as the mobile information terminal 71 and the personal computer 72 function as receiving means.

The water presented in the prescription can be easily produced by an electrolytic water production device. That is, the user can easily consume water suitable for his or her body by operating the electrolytic water production device while referring to the prescription.

It is preferred that the water prescribing system 1 further includes an electrolytic water production device 8 that can be connected to the Internet 7. The electrolytic water production device 8 produces electrolytic water by electrolyzing water.

The electrolytic water production device 8 of the present embodiment is connected to the server 2 or 2A via the Internet 7 and acquires prescriptions stored in the hard disk device and the like of the server 2 or 2A. Thereby, the electrolytic water production device 8 can automatically produce water suitable for the user based on the prescription, and the user of the electrolytic water production device 8 can easily consume water suitable for his or her body without performing complicated operations.

It should be noted that, regarding the main configuration, such as an electrolytic cell of the electrolytic water production device 8, it can be configured to be the same as that of the device disclosed in the Patent Literature 1, for example. It is preferred that the electrolytic water production device 8 of the present embodiment includes a communication unit that can be connected to the Internet 7. The electrolytic water production device 8 may be configured to be connectable to the Internet 7 via the mobile information terminal 71 or the like.

Figure 7:
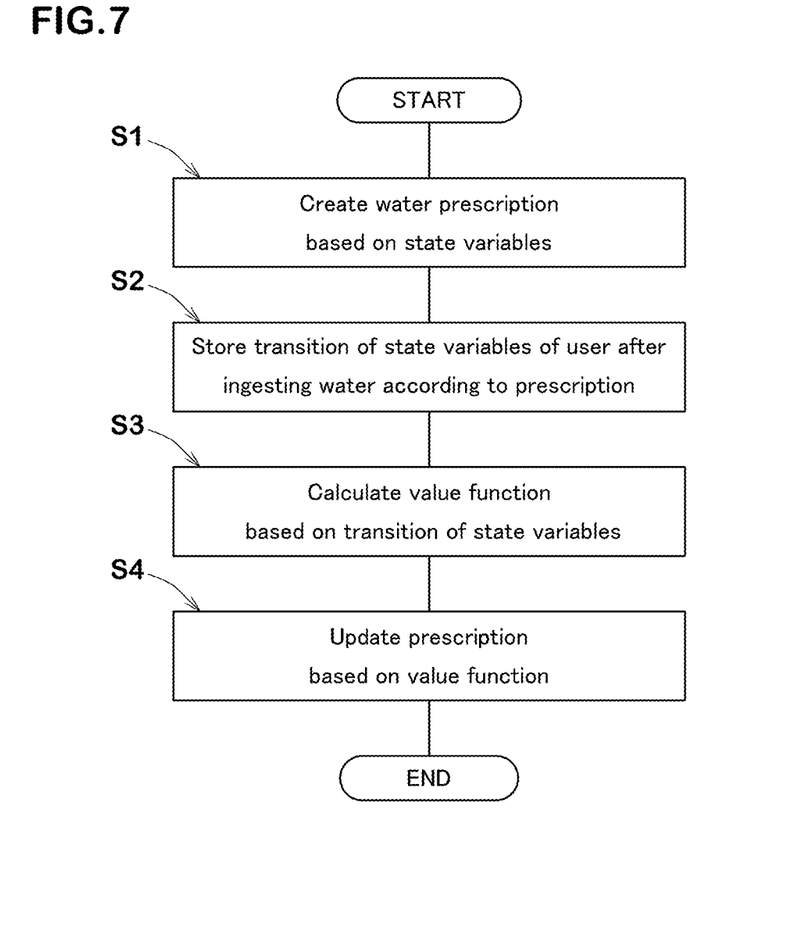
FIG. 7 A flowchart showing a process by which the server of FIG. 6 produces a prescription.

FIG. 7 shows a processing procedure in which the server 2A creates a prescription. Each of the steps in FIG. 7 is accomplished by executing a water prescribing program. That is, the water prescribing program is a program for causing a computer device to execute each of the steps, and is stored in various storage media readable by a computer device such as a magnetic disk, an optical disk, a nonvolatile memory, and the like of a hard disk device, for example. The server 2A accomplish various functions by reading the water prescribing program stored in the storage medium and executing each step.

In FIG. 7, in a first step S1, the prescription unit 22 creates a water prescription suitable for the user based on the state variables. The state variables are information regarding the physical constitution and health condition stored for each of a plurality of persons including the user. The state variables are stored in the state storage unit 21 in advance before the execution of the first step S1. The state variables may be stored in the state storage unit 21 by the server 2A executing the program, or may be stored in the state storage unit 21 manually by the administrator of the water prescribing system 1 or the like.

The first step S1 may include a step of applying each user's state variables to the learning model 3. It should be noted that by executing the first step S1, the operation of the server 2 ends.

In a second step S2, the transition of the state variables of the user after ingesting the water according to the prescription is stored in the state storage unit 21. The second step S2 may include a step of prompting the user or the administrator to input the transition of the state variables by an image, sound, or the like.

In a third step S3, the value calculation unit 24 calculates the value function based on the transition of the state variables. The third step S3 may include a step in which the reward calculation unit 26 calculates a reward based on the transition of the state variables. In this case, the value calculation unit 24 calculates the value function based on the reward.

In a fourth step S4, the update unit 25 updates the prescription based on the value function. This makes it possible to create prescriptions that properly reflect the transitions in the state variables.

While detailed description has been made of the water prescribing system and the water prescribing program of the present invention, the present invention can be embodied in various forms without being limited to the illustrated specific embodiment described above. In other words, it suffices as long as the water prescribing system includes the state storage unit 21 which stores the state variables relating to the physical constitution and health condition for each of a plurality of people including the user, and the prescription unit 22 which creates a water prescription suitable for the user based on the state variables.

In addition, it suffices as long as the water prescribing program is configured at least to cause the computer to perform the first step S1 to create the water prescription suitable for the user based on the state variables relating to the physical constitution and health condition stored in advance for each of a plurality of persons including the user.

Description of the Reference Signs

1: water prescribing system
2: server
2A: server
3: learning model
7: Internet
8: electrolytic water production device
21: state storage unit
22: prescription unit
23: model storage unit
24: value calculation unit
25: update unit
26: reward calculation unit
31a: state variable
31b: state variable
31c: state variable
33a: prescription
33b: prescription
33c: prescription
71: mobile information terminal
72: personal computer

The invention claimed is:

1. A water prescribing system comprising:
  a state storage unit provided in a server connectable to the Internet and configured to store a state variable relating to a physical constitution and health condition for each of a plurality of persons including a user;
  a prescription unit provided in the server and configured to create a prescription of water suitable for the user based on the state variable; and
  an electrolytic water production device for producing electrolytic water by electrolyzing water, wherein
  the prescription includes at least one of a pH value, a dissolved hydrogen concentration, a redox potential, and a temperature,
  the electrolytic water production device is connected with the server and produces the electrolytic water according to the prescription,
  the state storage unit stores transition of the state variable of the user after ingesting the electrolytic water according to the prescription, and
  the prescription unit has a value calculation unit for calculating value function relating to effect of the electrolytic water on the state variable based on the transition of the state variable and an update unit for updating the prescription based on the value function.

2. The water prescribing system according to claim 1, wherein
the state variable includes at least one of age, sex, height, weight, waist circumference, body temperature, blood pressure, blood test results, body fat percentage, visceral fat mass, basal metabolism, medical history, exercise history, alcohol intake, tobacco intake, and genetic information of each user.

3. The water prescribing system according to claim 1, wherein the prescription unit has a model storage unit for storing a learning model for creating the prescription suitable for the state variable and applies the state variable of each user to the learning model to create the prescription.

4. The water prescribing system according to claim 1, wherein
the prescription unit further includes a reward calculation unit for calculating a reward based on the transition of the state variable, and
the value calculation unit updates the value function based on the reward.

5. The water prescribing system according to claim 4, wherein the reward calculation unit gives the reward, having a positive value, when the state variable has changed favorably with regard to each user, and gives the reward, having a negative value, when the state variable has changed poorly with regard to each user.

6. The water prescribing system according to claim 3, wherein the learning model includes a neural network.

7. The water prescribing system according to claim 1, further comprising:
a transmission means which is connected to the server and transmits the state variable to the server.

* * * * *